US011103292B2

(12) United States Patent
Hachem et al.

(10) Patent No.: US 11,103,292 B2
(45) Date of Patent: Aug. 31, 2021

(54) BONE CERCLAGE CONSTRUCTS AND METHODS

(71) Applicant: Arthrex, Inc., Naples, FL (US)

(72) Inventors: Abdul Ilah Hachem, Barcelona (ES); Alexander Campagnoli, Aschheim (DE)

(73) Assignee: ARTHREX, INC., Naples, FL (US)

( * ) Notice: Subject to any disclaimer, the term of this patent is extended or adjusted under 35 U.S.C. 154(b) by 328 days.

(21) Appl. No.: 16/373,947

(22) Filed: Apr. 3, 2019

(65) Prior Publication Data

US 2020/0315677 A1   Oct. 8, 2020

(51) Int. Cl.
| | | |
|---|---|---|
| *A61B 17/56* | (2006.01) |
| *A61B 17/58* | (2006.01) |
| *A61B 17/82* | (2006.01) |
| *A61F 2/30* | (2006.01) |
| *A61B 17/06* | (2006.01) |
| *A61B 17/88* | (2006.01) |
| *A61B 17/16* | (2006.01) |
| *A61B 17/04* | (2006.01) |

(52) U.S. Cl.
CPC ........ *A61B 17/82* (2013.01); *A61B 17/06166* (2013.01); *A61B 17/1684* (2013.01); *A61B 17/8861* (2013.01); *A61B 17/8869* (2013.01); *A61B 17/1615* (2013.01); *A61B 2017/0496* (2013.01)

(58) Field of Classification Search
CPC combination set(s) only.
See application file for complete search history.

(56) References Cited

U.S. PATENT DOCUMENTS

| | | | |
|---|---|---|---|
| 8,257,359 B2 | 9/2012 | Burkhart et al. |
| 8,540,737 B2 | 9/2013 | Chudik |
| 9,402,650 B2 | 8/2016 | Boileau et al. |
| 10,172,703 B2 | 1/2019 | Adams et al. |
| 2005/0107797 A1 | 5/2005 | Romeo |
| 2014/0277185 A1* | 9/2014 | Boileau ................. A61B 17/02 606/300 |

FOREIGN PATENT DOCUMENTS

RU        2610861 C2      4/2015

OTHER PUBLICATIONS

E. Taverna, MD; "Arthroscopic Bone Graft Procedure for Anterior Inferior Glenohumeral Instability", European Shoulder Technique Guide, smith&nephew, 12 pgs.

* cited by examiner

*Primary Examiner* — Sameh R Boles
(74) *Attorney, Agent, or Firm* — Potomac Law Group, PLLC

(57) ABSTRACT

Cerclage constructs, systems, kits and methods of cerclage repairs are disclosed. A cerclage construct can create a repair without metal cerclage and cabling (metal wires, cables, etc.) and/or metal components (metal fittings, screws, etc.). A cerclage construct includes a plurality of interconnected flexible strands that secure a first bone (bone graft or bone block) to a second bone (bone graft or bone block) with a simple and compact design. The cerclage construct is a flexible, tensionable construct that eliminates the need for metal components in a fracture repair.

7 Claims, 13 Drawing Sheets

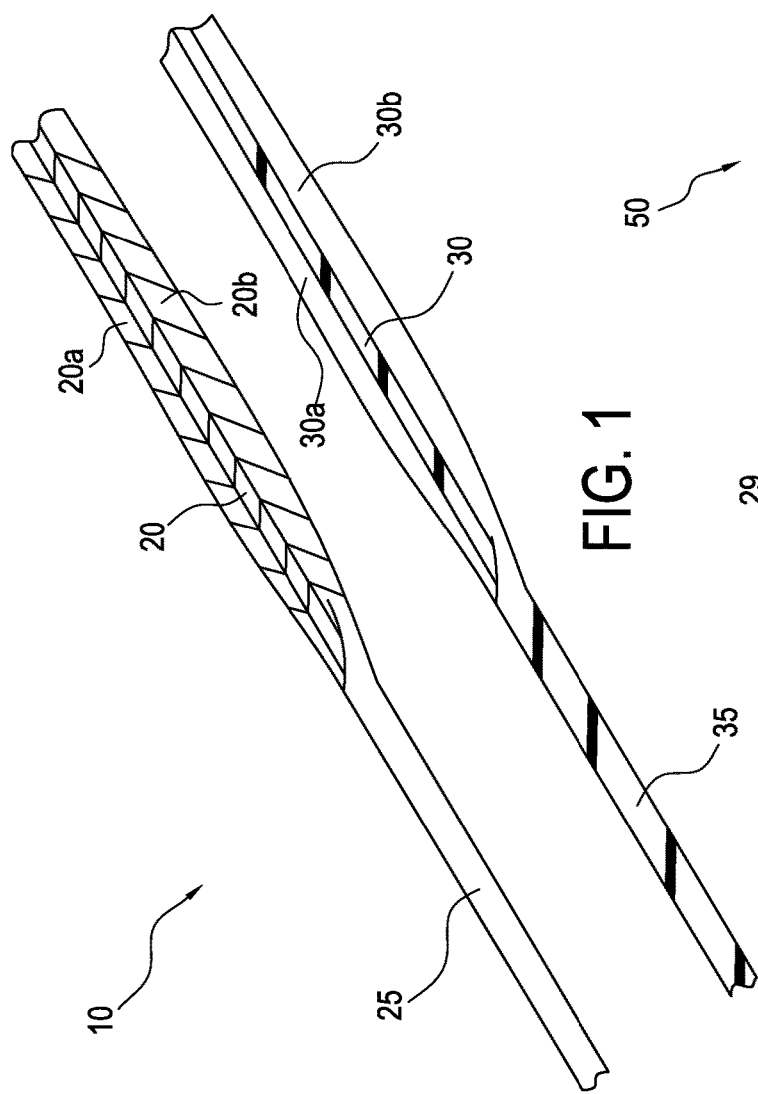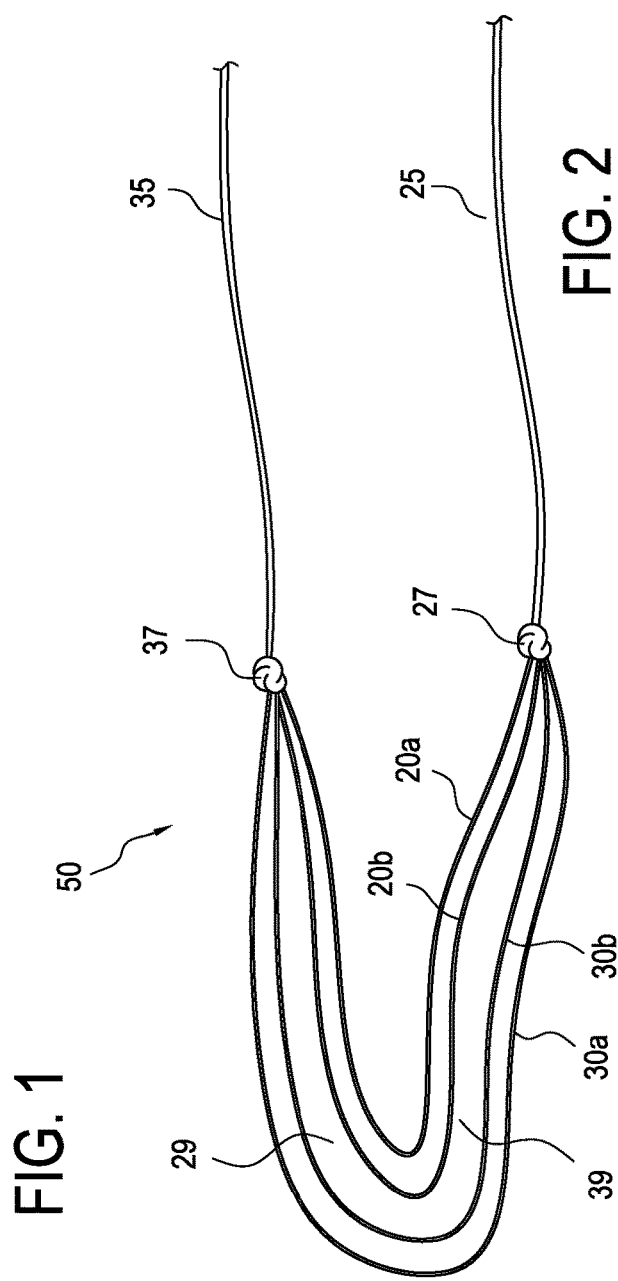

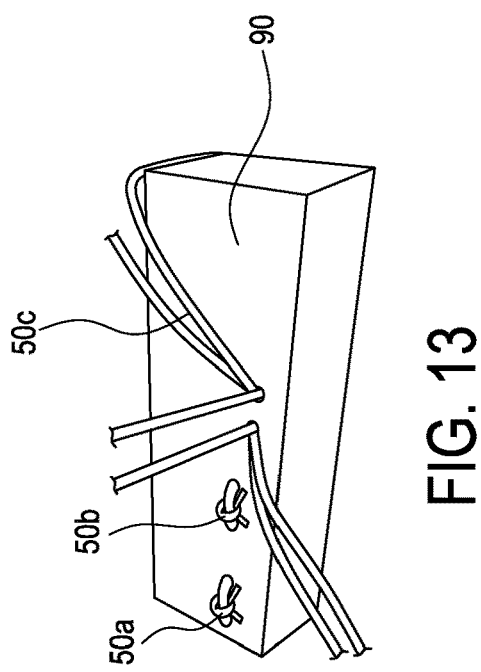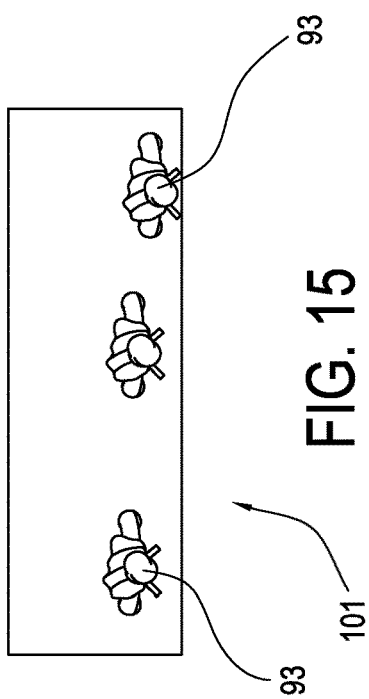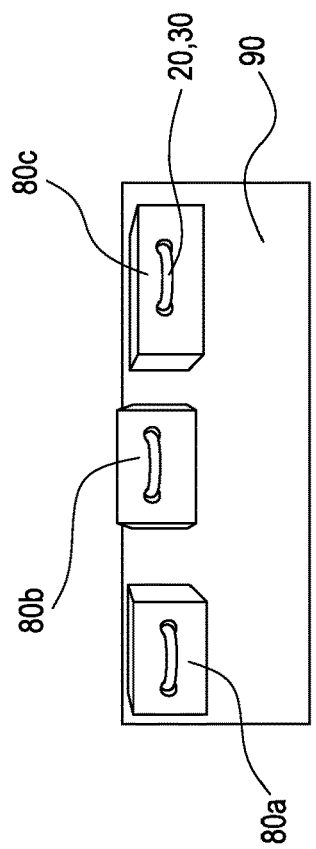

BONE CERCLAGE CONSTRUCTS AND METHODS

BACKGROUND

The disclosure relates to the field of surgery and, more specifically, to apparatus, systems, kits and methods for reconstructive surgeries.

SUMMARY

Cerclage constructs, systems, assemblies, kits and methods of cerclage repairs are disclosed. A cerclage construct can create a repair without metal cerclage and cabling (metal wires, cables, etc.) and/or metal components (metal fittings, screws, buttons, suture-button constructs, etc.). A cerclage construct includes interconnected flexible strands that secure a first bone (bone graft or bone block) to a second bone (bone graft or bone block) with a simple and compact design. In an embodiment, a bone block cerclage repair system includes interconnected cerclage suture tapes, or combination of suture tapes and sutures, to secure a bone block or graft to the glenoid. The bone block cerclage construct confers wide footprint compression similar to bone plate compression, and provides strong and stable fixation. The cerclage construct is a flexible, tensionable construct that eliminates the need for metal components in a fracture repair.

Bone cerclage methods are also disclosed. A first bone/graft is secured to a second bone/graft with a flexible, tensionable surgical construct that includes a plurality of flexible strands. In an embodiment, bone block cerclage is conducted with a flexible, tensionable surgical construct that includes a plurality of cerclage sutures and no metal wires or cables. In an embodiment, a plurality of flexible sutures or tapes (or combinations thereof) are passed through bones. In an embodiment, a plurality of flexible sutures or tapes (or combinations thereof) are passed through bone tunnels to secure a first bone or graft to a second bone or graft, or to hold bony fragments together, to allow them to heal. In an embodiment, bone loss in glenohumeral dislocation or chronic glenohumeral dislocation/subluxation is reduced by securing a preshaped bone graft with a plurality of interconnected cerclage suture tapes with the ability to symmetrically tension all suture tapes.

BRIEF DESCRIPTION OF THE DRAWINGS

FIG. 1 illustrates a cerclage assembly according to an exemplary embodiment.

FIG. 2 illustrates a cerclage construct with the assembly of FIG. 1.

FIGS. 13-15 illustrate steps of another exemplary method of bone cerclage with cerclage constructs.

DETAILED DESCRIPTION

Figure 3:
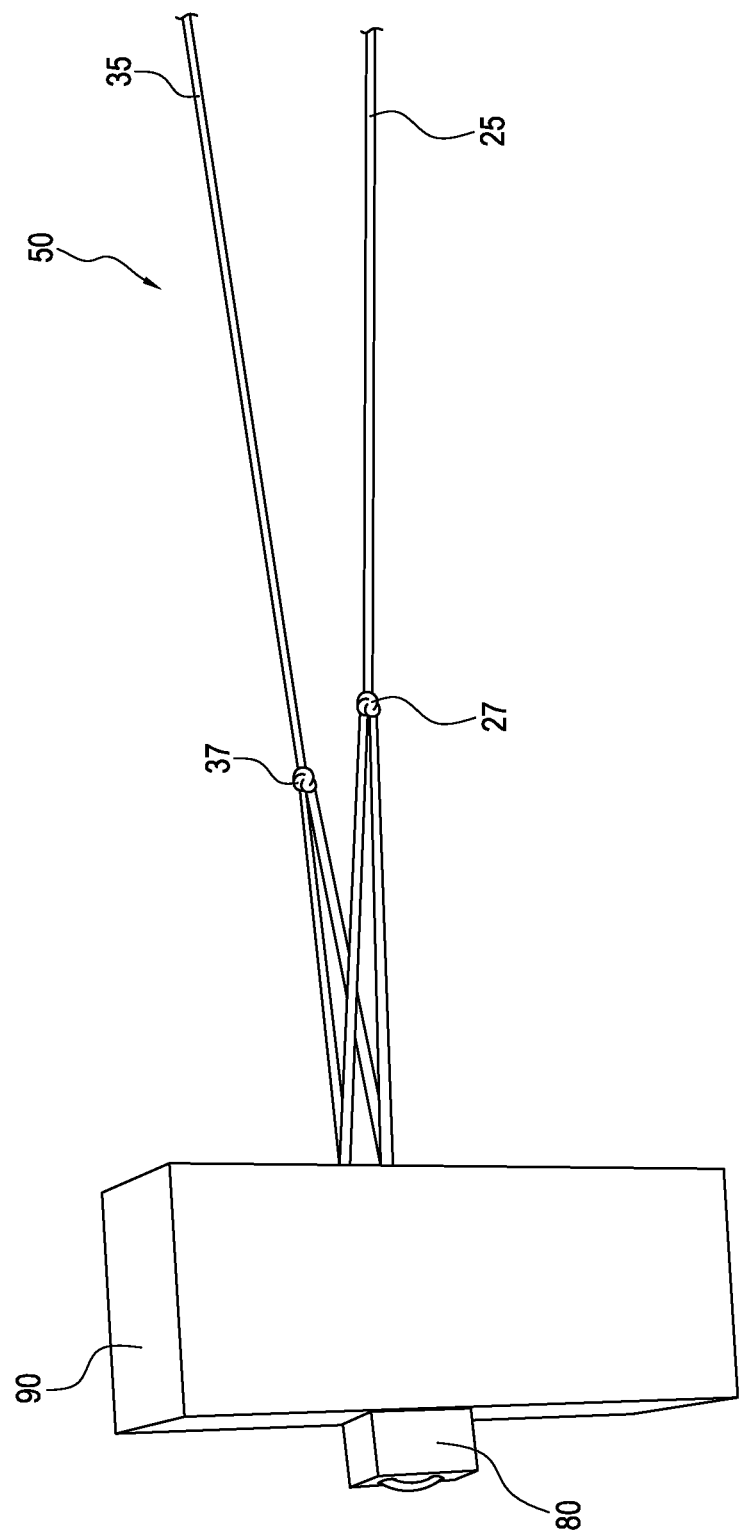
FIG. 3 illustrates another view of a cerclage construct.

The disclosure provides constructs, systems, assemblies, kits and methods for bone block cerclage repairs such as glenohumeral instability.

Cerclage constructs, systems, assemblies, kits and methods of tissue repairs are disclosed. A cerclage construct can create a repair without metal cerclage and cabling (metal wires, cables, etc.) and/or metal components (metal fittings, buttons, screws, anchors, buttons, suture-button constructs, etc.) and/or absorbable components (such as bioabsorbable screws). A cerclage construct includes a plurality of interconnected flexible strands (cerclage strands) that secure one or more bones (grafts or bone blocks) to one or more bones (grafts or bone blocks) with a simple and compact design. The cerclage strands are flexible strands in the form of sutures, tapes, suture chains, yarns, ribbons, or combinations of such, among many others.

In an embodiment, the flexible strands are two or more free sutures or free tapes. In an embodiment, the flexible strands are flat tapes. In an embodiment, two or more flexible strands may terminate in a single tail or single end to facilitate insertion and passage through bone tunnels.

The flexible strands may be made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). The flexible strands may be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein.

The cerclage strands may also include, and be manufactured with, any kind of flexible strands that can allow the flexible strands to be interconnected and/or interlinked and/or joined during the cerclage procedure, eliminating the need for any metallic structure.

The cerclage strands may be also provided with a connecting mechanism (securing mechanism or joining mechanism) to allow other strands to connect thereto. The connecting mechanism may include (or be in the form of) a knot, half-knot, raking hitch knot, loop, splice, eyelet, etc., or any similar structure that allows connecting two or more strands. The connecting mechanism may be, for example, a pre-configured knot or may include a half-knot with a flexible sheath between the cinch, the sheath being provided with a flexible strand passing through the sheath and provided with two loops to pass single limbs. Alternatively, once the free sutures and/or tapes have passed through bone tunnels, the sutures may be interconnected by, for example, taking the free limbs of each suture and creating a knot with the other suture (for example, a racking hitch knot). In other exemplary embodiments, the strands may be also joined/interconnected/connected by splicing, fusion, gluing or by other methods or combined methods known in the art.

In an exemplary embodiment, a bone block cerclage construct (repair system) includes two or more cerclage strands in the form of free single strands (such as sutures, tapes, filaments, fibers, etc. or combinations thereof) to secure one or more bone blocks or grafts to the glenoid. The free strands may be provided with a connecting mechanism (securing mechanism or joining mechanism) to allow the other strands to connect thereto. The connecting mechanism may include (or be in the form of) a knot, half-knot, raking hitch knot, loop, splice, eyelet, etc., or any similar structure that allows connecting two or more strands, as detailed above.

The free strands may be provided with a pre-configured connecting mechanism. For example, one or more free strands may have a pre-configured knot already made as a connecting mechanism. The knots may be configured manually. The knots may be formed in situ, if desired. In one embodiment, the free strands are passed through bone tunnels and then the strands are interconnected to form a cerclage construct. The cerclage construct confers wide footprint compression similar to bone plate compression, and provides strong and stable fixation. The cerclage construct is a flexible, tensionable construct that eliminates the need for any metal components in a fracture repair. In an embodiment, the cerclage construct consists essentially of two sutures or tapes interconnected after passage through bone tunnels.

In an exemplary embodiment, a bone block cerclage construct (repair system) includes two or more cerclage sutures or cerclage tapes, or combination of suture and tapes, to secure a bone block or graft to the glenoid. The sutures and/or tapes are free strands that are interconnected through a connecting mechanism to form a cerclage construct. The free sutures and/or tapes are passed through bone tunnels and then the sutures are interconnected by, for example, taking the free limbs of each suture and creating a knot with the other suture (for example, a racking hitch knot). The cerclage construct confers wide footprint compression similar to bone plate compression, and provides strong and stable fixation. The cerclage construct is a flexible, tensionable construct that eliminates the need for any metal components or metal-like components in a fracture repair. The bone tunnels are formed through both the glenoid and the bone block or graft.

In an exemplary embodiment, a bone block cerclage construct (repair system) includes two interconnected cerclage sutures (cerclage strands), or combination of suture tapes and sutures, to secure a bone block or graft to the glenoid. The cerclage sutures may include two or more lengths of suture tapes (flexible strands) terminating in a single end or single tail. The cerclage sutures may include a connecting mechanism to allow other cerclage sutures to connect/interconnect thereto. As detailed above, the connecting mechanism may be, for example, a pre-configured knot or may include a half-knot with a sheath between the cinch, the sheath being provided with a flexible strand passing through the sheath and provided with two loops to pass single limbs. The bone block cerclage construct confers wide footprint compression similar to bone plate compression, and provides strong and stable fixation. The cerclage construct is a flexible, tensionable construct that eliminates the need for any metal components or metal-like components in a fracture repair.

Methods of tissue repairs and reconstructive surgeries are also disclosed. A first tissue is secured to a second tissue with a flexible, tensionable surgical construct that includes a plurality of interconnected cerclage strands. In an embodiment, bone block cerclage repair is conducted with a flexible, tensionable surgical construct that includes a plurality of flexible strands and no metal wires or cables. In an exemplary embodiment, two or more interconnected flexible sutures or tapes (or combinations thereof) are employed to secure one or more first bones or grafts to one or more second bones or grafts, or to hold bony fragments together, to allow them to heal. In an embodiment, bone loss in glenohumeral dislocation or chronic glenohumeral dislocation/subluxation is reduced by securing a preshaped bone graft with two interconnected suture tapes with the ability to symmetrically tension both suture tapes. The plurality of flexible strands pass through one or more first bone tunnels and through one or more second bone tunnels at least two times (once in a first direction and once in a second direction, which is opposite the first direction).

In an embodiment, a bone block cerclage construct (repair system) includes two cerclage strands (cerclage sutures) to secure a bone block/graft to the glenoid. The repair system improves the bone loss in traumatic glenohumeral dislocation or chronic glenohumeral dislocation/subluxation by securing a preshaped bone graft with two cerclage sutures. Each of the cerclage sutures may include two or more flexible strands in the form of tapes, for example two or more FiberTape® suture tapes. The cerclage sutures are interconnected to each other, conferring the ability to symmetrically tension both strands/sutures. The suture tapes are provided with a connecting mechanism (joining, securing or interconnecting mechanism) to allow other of the suture tapes to attach thereto. In an embodiment, the cerclage sutures include two FiberTape® cerclage sutures, wherein each of the FiberTape® cerclage suture has a connecting mechanism to allow the other of the FiberTape® cerclage suture to attach thereto and connect to each other (interconnect). In an embodiment, the cerclage construct consists of two FiberTape® cerclage sutures. In an embodiment, the cerclage construct consists essentially of two FiberTape® cerclage sutures.

In an embodiment, two cerclage strands such as two sutures, for example, two FiberTape® cerclage sutures, are employed to hold bones together. Using cerclage sutures in lieu of metal or absorbable screws employed with suture makes the technique easier and more reproducible, while avoiding intra-operative and post-operative complications. During the exemplary bone cerclage technique described below, two FiberTape® cerclage sutures are passed through two bone tunnels (for example, 2.4 mm bone tunnels) formed within two bone fragments using a posterior guide. A tensioner may be employed for the FiberTape® cerclage sutures. In addition, a plurality of fixation devices (such as one or more anchors) may be employed to reattach the labrum to the capsule.

As detailed below, a unique feature of the disclosed cerclage technique is using two or more flexible strands (such as FiberTape® cerclage sutures) interconnected to each other; the interconnected strands confer the ability for symmetrically tensioning all strands. The disclosed technique offers higher, adjustable compression of the bone block and fixation without metal components/screws. The disclosed technique is also simpler and less invasive since smaller bone tunnels are needed. The cerclage mechanism detailed below attaches bone grafts/blocks to the glenoid with no metal construct, wider footprint compression (similar to a bone plate), and with a strong and stable fixation.

Two or more flexible materials (for example, sutures, suture tapes, suture chains, filaments, fibers, strands, etc.) are interconnected to each other to form a tensionable construct. The flexible materials are passed at least twice through two or more small tunnels/holes/passages formed within the bone fragments to be attached and then interconnected.

A method of cerclage repair comprises inter alia the steps of passing two or more flexible strands through first and second bone segments (bones, bone blocks, bone grafts, bone fragments); interconnecting the two or more flexible strands to form a cerclage construct; and tensioning the cerclage construct, all steps being conducted without any metallic components and/or structures as part of the cerclage repair.

A method of providing a compressive force across a repair (bone fragments or body tissues, etc.) comprises inter alia the steps of: (i) passing an assembly with two or more flexible strands through tunnels formed into two or more bone fragments to be attached; (ii) interconnecting at least two of the flexible strands to form a tensionable construct; and (iii) pulling on the free ends of the tensionable construct to tension the entire construct and fix it at the same time. The flexible strands may be suture strands or tapes and may be interconnected by placing a free end of one strand into a suture loop of another strand, for example. The flexible strands may be suture strands or suture tapes and may be interconnected by manually connecting the sutures or tapes by forming a knot, for example. The knot may be a sliding knot. The flexible strands may be provided with a connecting mechanism (joining or securing or interconnecting mechanism) to connect with other flexible strands. The flexible strands may be provided with a pre-configured connecting mechanism. The flexible strands may also be provided without any connecting mechanism and, instead, they may be connected manually after passage through bone tunnels.

A method of providing a compressive force across a repair (bone fragments or body tissues, etc.) comprises inter alia the steps of: (i) passing an assembly with two or more flexible materials through tunnels formed into bone fragments to be attached, at least two of the flexible materials being each provided with a connecting mechanism; (ii) interconnecting the at least two of the flexible materials through or with the connecting mechanism, to form a tensionable construct; and (iii) pulling on the free ends of the tensionable construct to tension the entire construct and fix it at the same time.

According to another embodiment, the present disclosure provides a metal-free cerclage repair by inter alia the steps of: (i) providing a first bone block or bone adjacent a second bone block or bone; (ii) passing (in at least two different directions) a cerclage construct through tunnels formed through the first and second bone blocks or bones, the cerclage construct including two FiberTape® cerclage strands, each provided with a connecting mechanism (joining or securing or interconnecting mechanism) to allow the other of the FiberTape® cerclage strands to be attached thereto; (iii) interconnecting/connecting the two FiberTape® cerclage strands to form a tensionable construct with two free ends and at least one continuous, flexible, adjustable loop; and (iv) pulling on the free ends to tension the cerclage construct and approximate the bone block to the bone. The connecting mechanism may include a knot (for example, a pre-tied knot or a racking hitch knot) and/or a shuttling device (such as a Nitinol loop).

The cerclage constructs and methods of the present disclosure provide apparatus and methods for tissue repair, for example, bone to bone repair, or other tissue (such as graft) to bone repair. The surgical cerclage constructs allow for simplified cerclage repairs, and help simplify shuttling and managing of cerclage suture.

Figure 17:
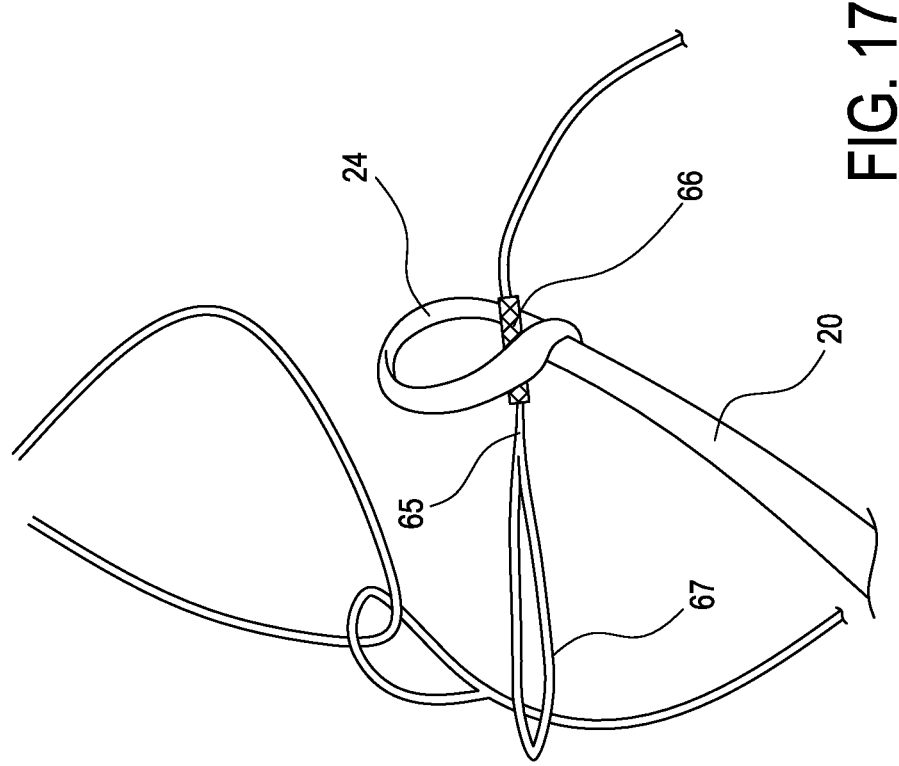
FIGS. 16 and 17 illustrate schematic views of a connecting mechanism.
Figure 16:
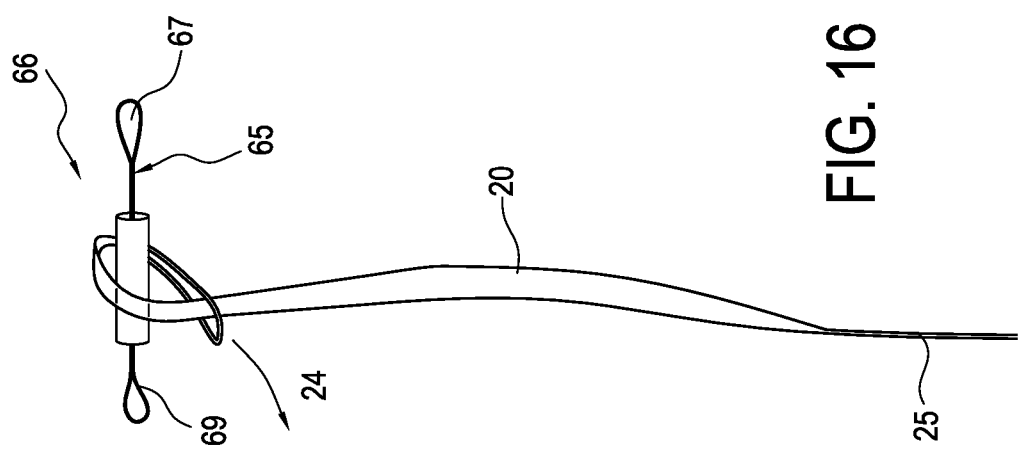
Figure 20:
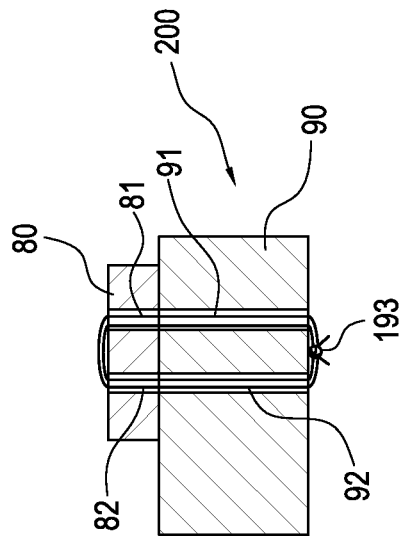
FIGS. 18-20 illustrate steps of another exemplary method of bone cerclage with cerclage constructs.
Figure 19:
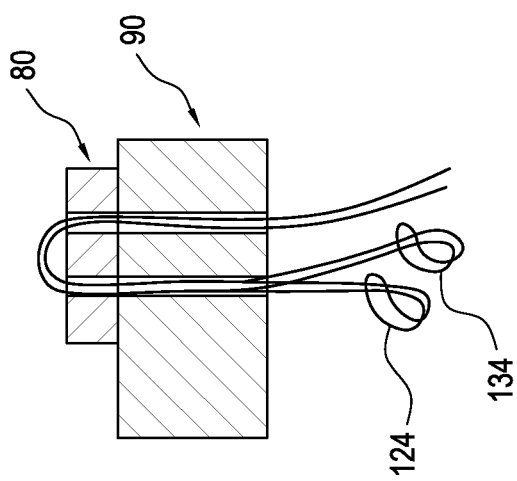
Figure 18:
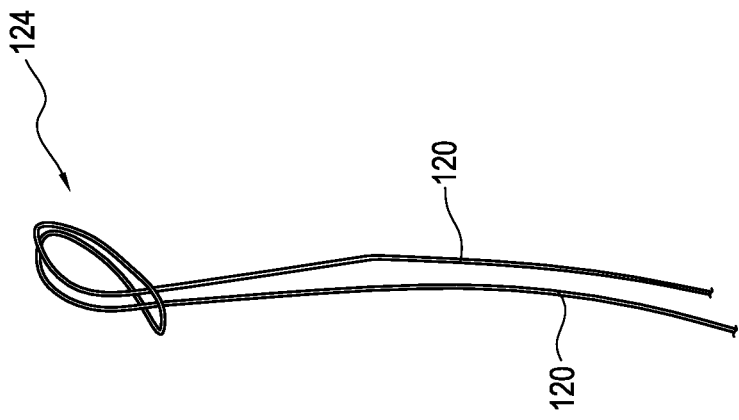

Referring now to the drawings, where like elements are designated by like reference numerals, FIGS. 1 and 2 illustrate structural components of surgical assembly 10 (cerclage assembly 10; cerclage system 10) and surgical construct 50 (cerclage construct 50; bone cerclage construct 50) of the present disclosure. FIG. 3 illustrates the surgical construct 50 of FIG. 2 assembled on a first bone block or bone secured to a second bone block or bone. FIGS. 4-12 illustrate steps of methods of tissue repair 100 with exemplary surgical construct 50. FIGS. 13-15 illustrate cerclage repair 101 of the present disclosure. FIGS. 16 and 17 illustrate schematic views of an exemplary connecting mechanism of the present disclosure. FIGS. 18-20 illustrate steps of another exemplary method of bone cerclage repair 200 with exemplary surgical cerclage constructs of the present disclosure.

FIG. 1 illustrates exemplary cerclage assembly 10 which includes a plurality of flexible cerclage strands 20, 30. FIG. 1 illustrate assembly 10 with only two exemplary flexible cerclage strands 20, 30; however, the disclosure is not limited to this embodiment and contemplates cerclage assemblies with any number of cerclage strands.

Cerclage assembly 10 includes cerclage strands 20, 30 which are in the form of elongated members, fibers, or materials 20, 30. The cerclage strands 20, 30 can include a single filament, or fiber, or can include multiple continuous filaments, segments or regions of filaments that have different configurations (for example, different diameters and/or different compositions). The filament regions/segments may each be homogenous (i.e., formed of a same material) or may be a combination of homogenous and heterogenous (i.e., formed of a plurality of materials). Exemplary materials may include suture, silk, cotton, nylon, polypropylene, polyethylene, ultrahigh molecular weight polyethylene (UHMWPE), polyethylene terephthalate (PET), and polyesters and copolymers thereof, or combinations thereof.

The cerclage strands 20, 30 may be cerclage tapes such as FiberTape® and/or TigerTape™ cerclage sutures or any ultra-high strength tapes of about 2 mm width and with similar structure as FiberWire® suture. The tapes provide broad compression and increased tissue cut-through resistance making it an excellent choice for knotless rotator cuff repair with the SpeedBridge™ and SpeedFix™ repair techniques. The taps are also useful for high demand applications like AC joint reconstruction and other areas where tissue pull-through may be a concern. FiberTape® and/or TigerTape™ cerclage sutures are formed of translucent suture that eliminates the need for wires and metal cables in fracture repairs.

In an exemplary embodiment only, and as shown in FIG. 1, the cerclage assembly 10 includes one FiberTape® cerclage tape 20 and one TigerTape™ cerclage tape 30, each formed of two flexible strands 20a, 20b, 30a, 30b terminating in a single end or tail 25, 35. In an exemplary embodiment, flexible strands 20a, 20b, 30a, 30b are suture tapes 20a, 20b, 30a, 30b that are swedged or joined or connected at each end to form tails/ends 25, 35 (as illustrated in FIG. 1). For simplicity, FiberTape® and TigerTape™ cerclage sutures 20, 30 are illustrated in two different colors, blue and white. FIG. 1 shows only the proximal end of cerclage strands 20, 30 (i.e., the end terminating in a single tail 25, 35). The distal end of the cerclage assembly 10 includes four flexible strands 20a, 20b, 30a, 30b. Single tail/end 25, 35 may be suture with a round cross-section.

The FiberTape® cerclage system is a strong, simple, and effective solution for replacing metal cables and wires traditionally used for fracture fixation. The low-profile, broad footprint of the FiberTape® cerclage suture provides superior compression and ultimate load compared to traditional metal cables and wires. In an embodiment, the system includes FiberTape® and TigerTape™ cerclage sutures, various passing instruments, tensioner, handle, and an instrument tray.

In the exemplary embodiment of FIG. 1, surgical assembly 10 includes cerclage strands 20, 30 with each including two similar flexible flat suture tapes 20a, 20b and 30a, 30b, respectively, connected at an end and terminating in tails 25, 35; however, the disclosure is not limited to this exemplary-only embodiment and contemplates embodiments wherein the flexible strands of the cerclage suture are formed of a plurality of monofilaments or multifilaments, which may have similar or different characteristics, sizes, shapes, properties, etc., depending on the intended application, and which may not terminate in a single tail or single end (i.e., the strands are two simple strands that are not combined or connected) before passage through bones or blocks/grafts. The lengths, sizes, properties and configurations of the cerclage strands 20, 30 and flexible strands 20a, 20b, 30a, 30b may be similar or different.

In an embodiment, flexible strands 20a, 20b, 30a, 30b are formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. In an embodiment, flexible strands 20a, 20b, 30a, 30b are made of fibers of ultrahigh molecular weight polyethylene (UHMWPE) or the Fiber-Wire® suture (disclosed in U.S. Pat. No. 6,716,234, the disclosure of which is hereby incorporated by reference in its entirety herein).

Strands 20, 30 may be connected in situ, after their passage through bone tunnels formed into bones to be connected. Strands 20, 30 may not be pre-configured with a connecting mechanism (securing or joining mechanism). In such case, strands 20, 30 may be connected manually, by attaching one strand to the other and forming a knot, for example a sliding knot, or by splicing one strand onto the other, or by other methods known in the art.

Alternatively, strands 20, 30 may be provided or pre-configured with a connecting mechanism (securing or joining mechanism). In an exemplary embodiment, each of cerclage strands 20, 30 may be provided with a connecting mechanism 22, 33 (securing or joining mechanism 22, 33) that allows attachment of the other of the cerclage strands 20, 30 to form cerclage construct 50 shown in FIG. 2. Although the disclosure will be detailed below with reference to strands 20, 30 pre-configured with a connecting mechanism, it must be understood that the invention is not limited to this exemplary embodiment only, and encompasses flexible strands that are not pre-configured with any connecting mechanism or similar structure.

In an exemplary embodiment, connecting mechanism 22, 33 may include a half knot 24, 34 and a shuttling device attached to the knot. These structures are schematically illustrated in FIGS. 16 and 17. Half knot 24 may be a pre-tied racking hitch knot 24 which is formed by Fiber-Tape® cerclage strand 20 that surrounds shuttling device 66. Shuttling device 66 may be in the form of a sheath 66 (flexible tubular member 66) that allows passage of a flexible strand 65 terminating in two loops 67, 69. Sheath 66 may be provided in between the half knot/cinch, as shown in FIGS. 16 and 17. Flexible strand 65 may be a simple suture with two loops that allow passing of limbs from other strands of the assembly 10. Sheath 66 may be a tubular member in the form of a sleeve that is formed of suture or similar material. Sheath 66 may include two open ends.

Passing one or more of the flexible strands 20a, 20b, 30a, 30b through the connecting mechanism 22, 33 of the other of the flexible strands 20a, 20b, 30a, 30b allows the flexible strands to be connected to each other and form knots 27, 37 and loops 29, 39 shown in FIG. 2. Once the single tail of one of the cerclage strands 20, 30 is loaded onto the loop of the shuttling device and then passed through the pre-tied racking hitch knot 24, 34 of the other one of the cerclage strands 20, 30, the tape portion of the flexible strand engages the pre-tied racking hitch knot 24, 34 and forms tied knots 27, 37 (FIG. 2).

Knots 27, 37 may be sliding knots. As detailed below, each of the suture swedge/tail will be cut to separate the two limbs (the two tails of FiberTape® cerclage suture) and the suture tapes are then knotted and tensioned with a tensioner, for example. Connecting mechanism 22, 33 may be also in the form of a splicing mechanism to allow splicing of one strand into/to another strand, or any other joining mechanism.

The cerclage construct 50 is a flexible, tensionable construct that eliminates the need for metal components in a fracture repair.

FIGS. 4-12 illustrate exemplary steps of a cerclage repair with assembly 10 and cerclage construct 50 of FIGS. 1 and 2. Tails 25, 35 of assembly 10 are inserted and passed through first and second bone tunnels 81, 82, 91, 92 (through-holes 81, 82, 91, 92; passages 81, 82, 91, 92) formed within a first bone block or bone 80 and a second bone block or bone 90. In an exemplary embodiment, first bone block or bone 80 is a bone graft 80 (pre-shaped bone graft 80), and the second bone block or bone 90 is glenoid. In an embodiment, the first bone block or bone 80 is coracoid (pre-shaped coracoid) and the second bone block or bone 90 is the glenoid.

Figure 4:
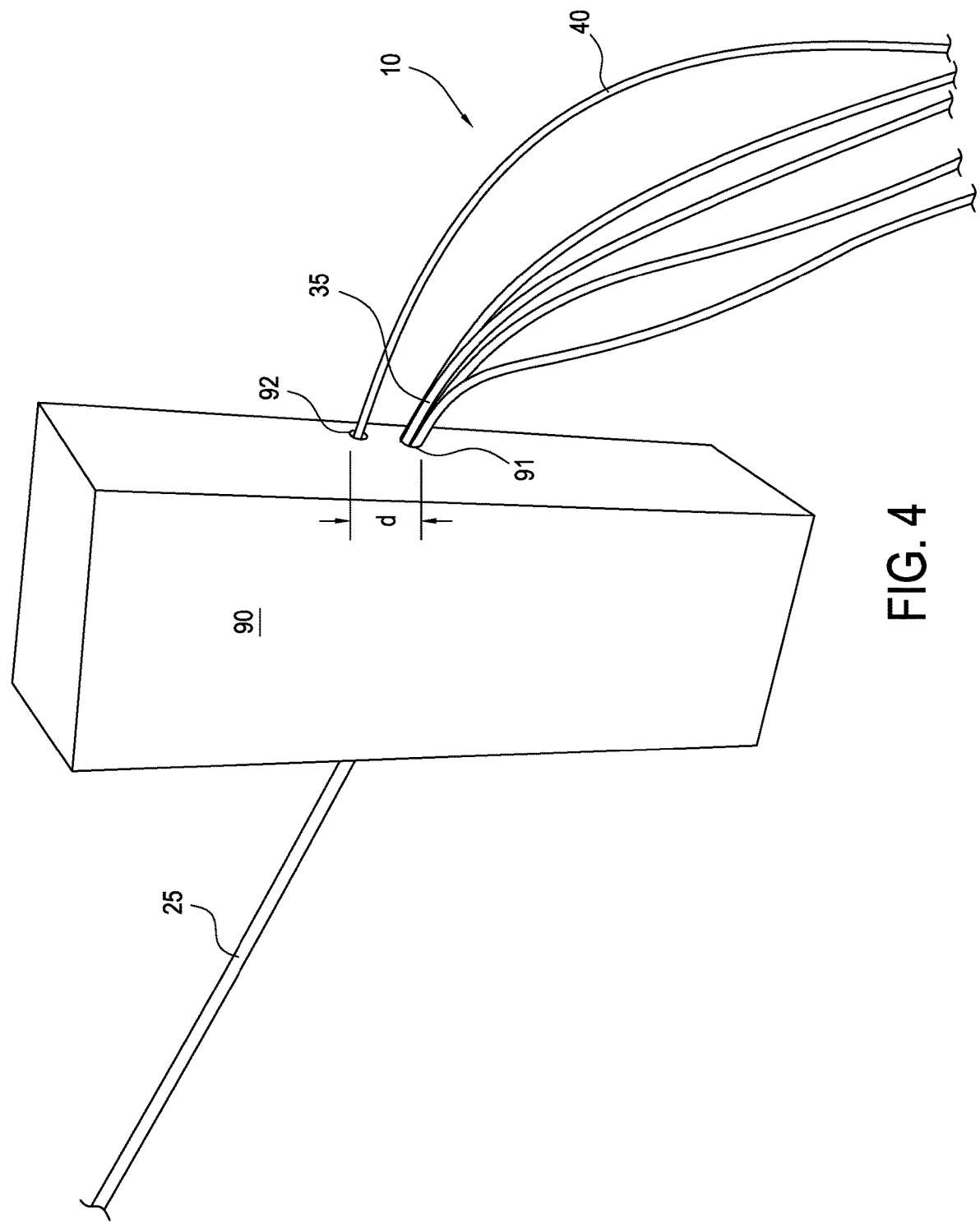
FIG. 4-12 illustrate steps of an exemplary method of bone cerclage with cerclage constructs.
Figure 5:
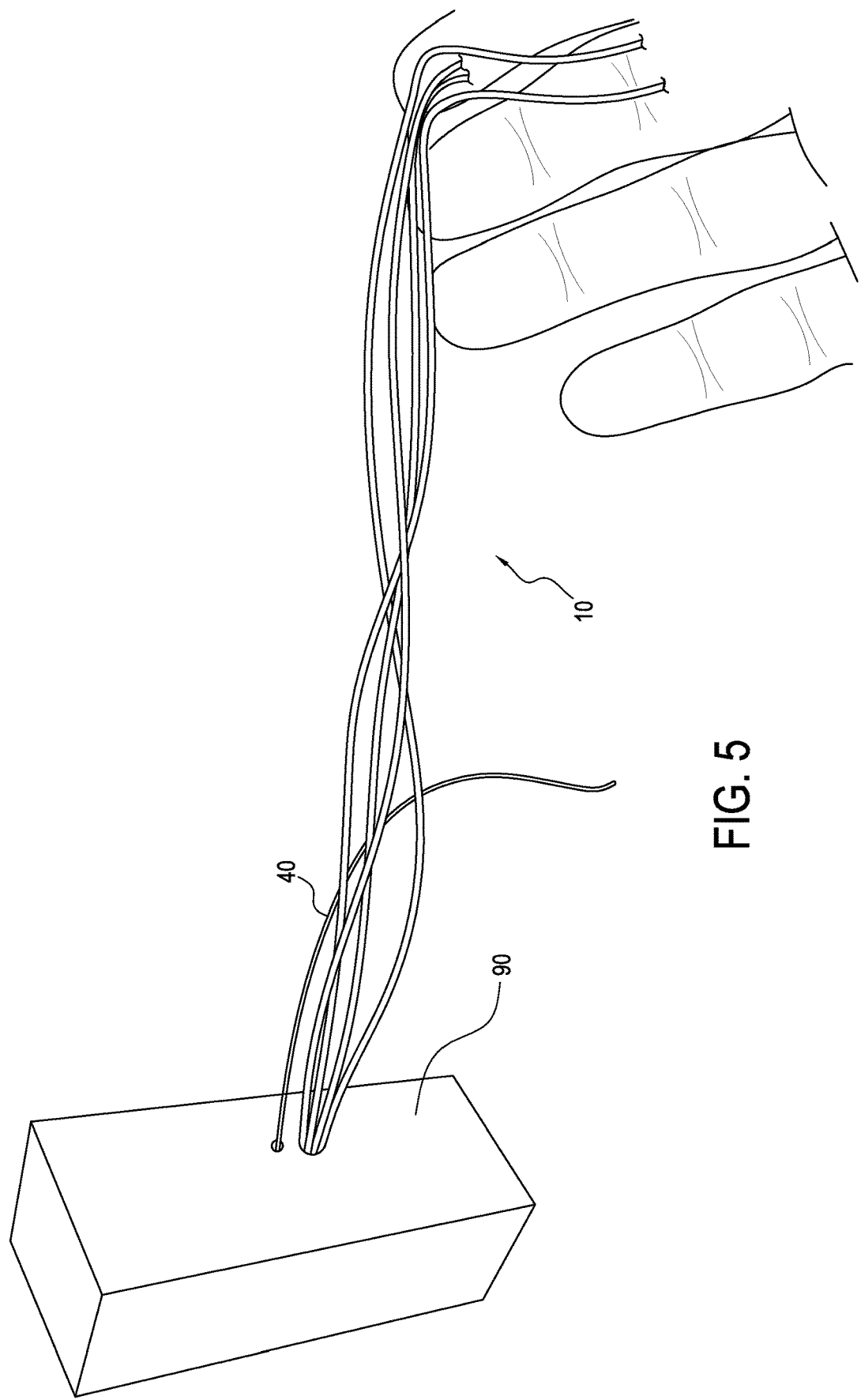

Bone tunnels or passages 81, 82, 91, 92 may be formed, for example, by placing the bone graft 80 onto/on adjacent the glenoid 90 and drilling the first and second bone blocks or bones 80, 90 to about 2.4 mm using a posterior guide. Bone tunnels 81, 91 form a continuous first bone tunnel and bone tunnels 82, 92 form a continuous second bone tunnel, which is spaced apart from the first bone tunnel by a distance "d" (FIG. 4).

Figure 6:
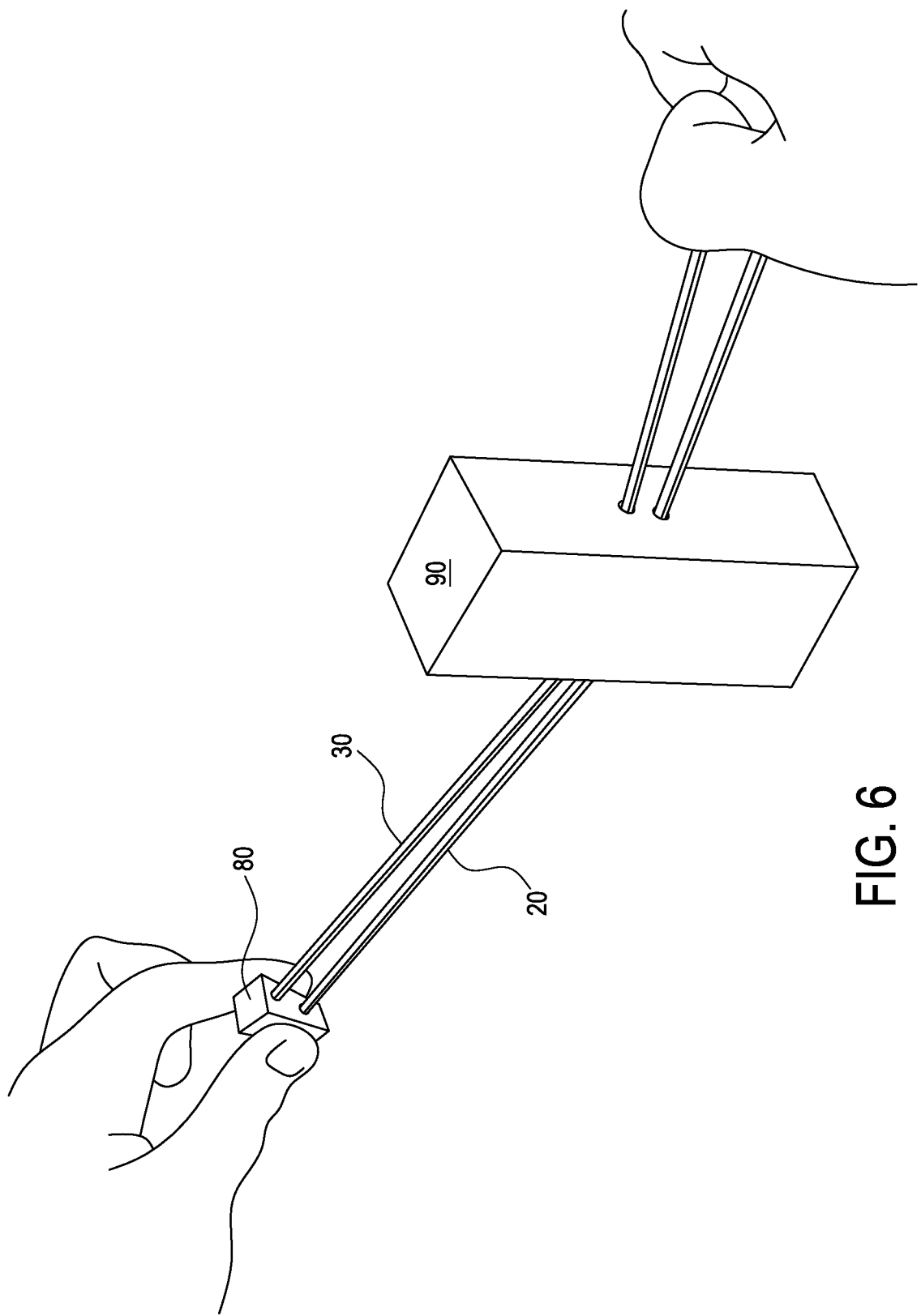

Assembly 10 is inserted and passed through bone tunnels 91, 81 (formed into glenoid and bone graft) in a first direction D1 (FIG. 12) and then through bone tunnels 82, 92 to exit the glenoid 90 (as shown in FIG. 6, for example) in a second direction D2 (FIG. 12), which is different from the first direction. First direction D1 may be opposite second direction D2. Insertion and passage of assembly 10 through the bone tunnels 91, 81 and then through bone tunnels 82, 92 may be conducted with a shuttling device or suture passing instrument such as a suture passer 40 (FIG. 4). Tails 25, 35 of cerclage assembly 10 are passed/looped through a loop of the suture passer 40 and then shuttled through the bone tunnels 91, 81, exit the bone block or bone 80 and then reenter the bone block 80 and the bone block 90 through bone tunnels 82, 92, exiting the bone block 90. Cerclage strands 20, 30 form a "U" shaped cerclage construct within the bone block 80 and glenoid 90, and on an exterior surface of the bone block 80. Cerclage strands 20, 30 are passed through the bones at least two times and in at least two different directions, a first direction (through bone tunnels 91, 81) and in a second direction (through bone tunnels 82, 92), the second direction being different from the first direction. In an embodiment, the first direction is opposite the second direction.

Pulling on the flexible strands 20a, 20b, 30a, 30b of cerclage strands 20, 30 allows bone graft 80 to be approximated to glenoid 90. Passing of assembly 10 through tunnels 81, 82, 91, 92 is conducted with suture passer 40 or any other shuttling instrument, for example, by passing single tails 25, 35 through a loop of a suture passer and then passing the suture passer (with the looped single tails 25, 35 of the cerclage sutures 20, 30) through the tunnels.

Figure 7:
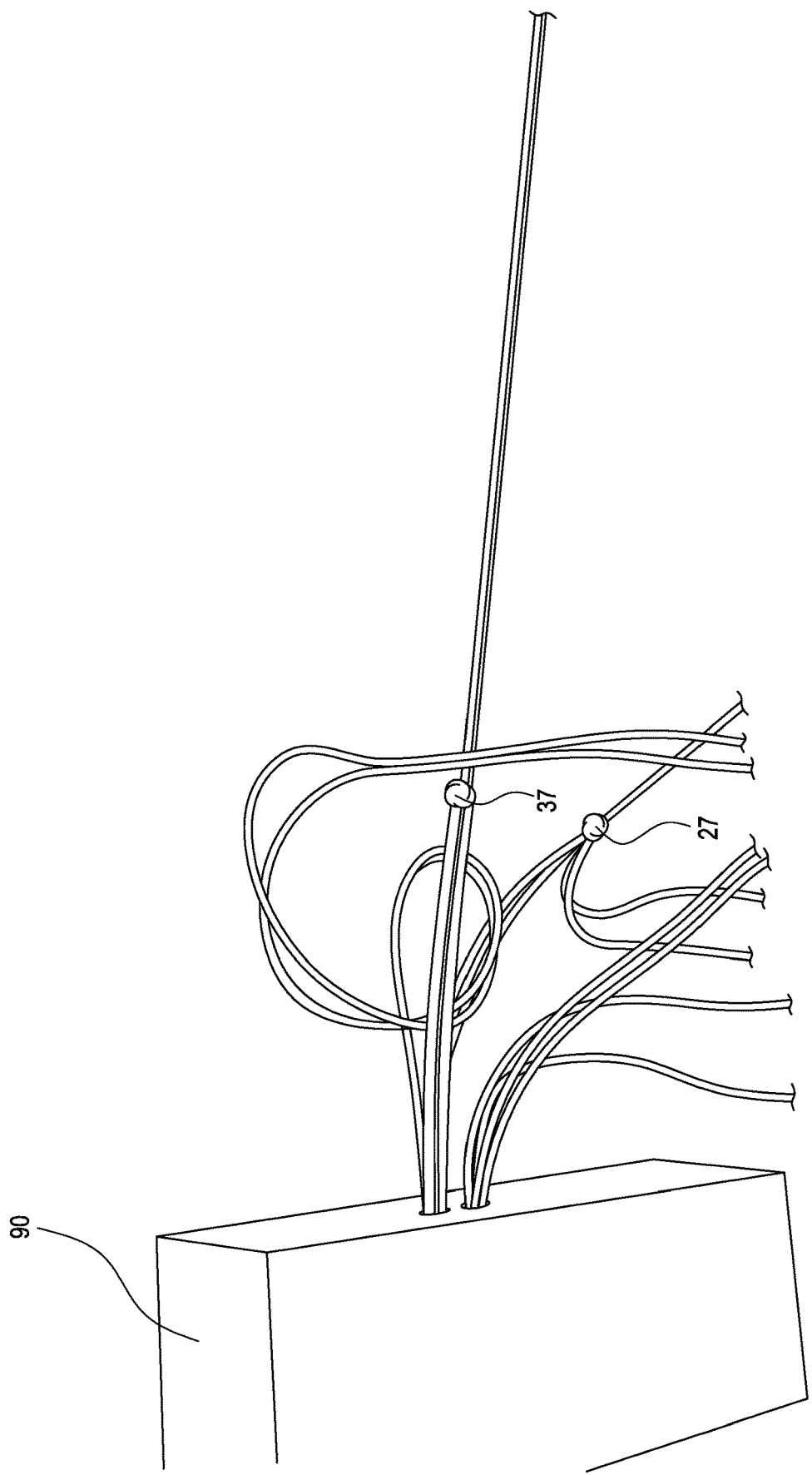
Figure 8:
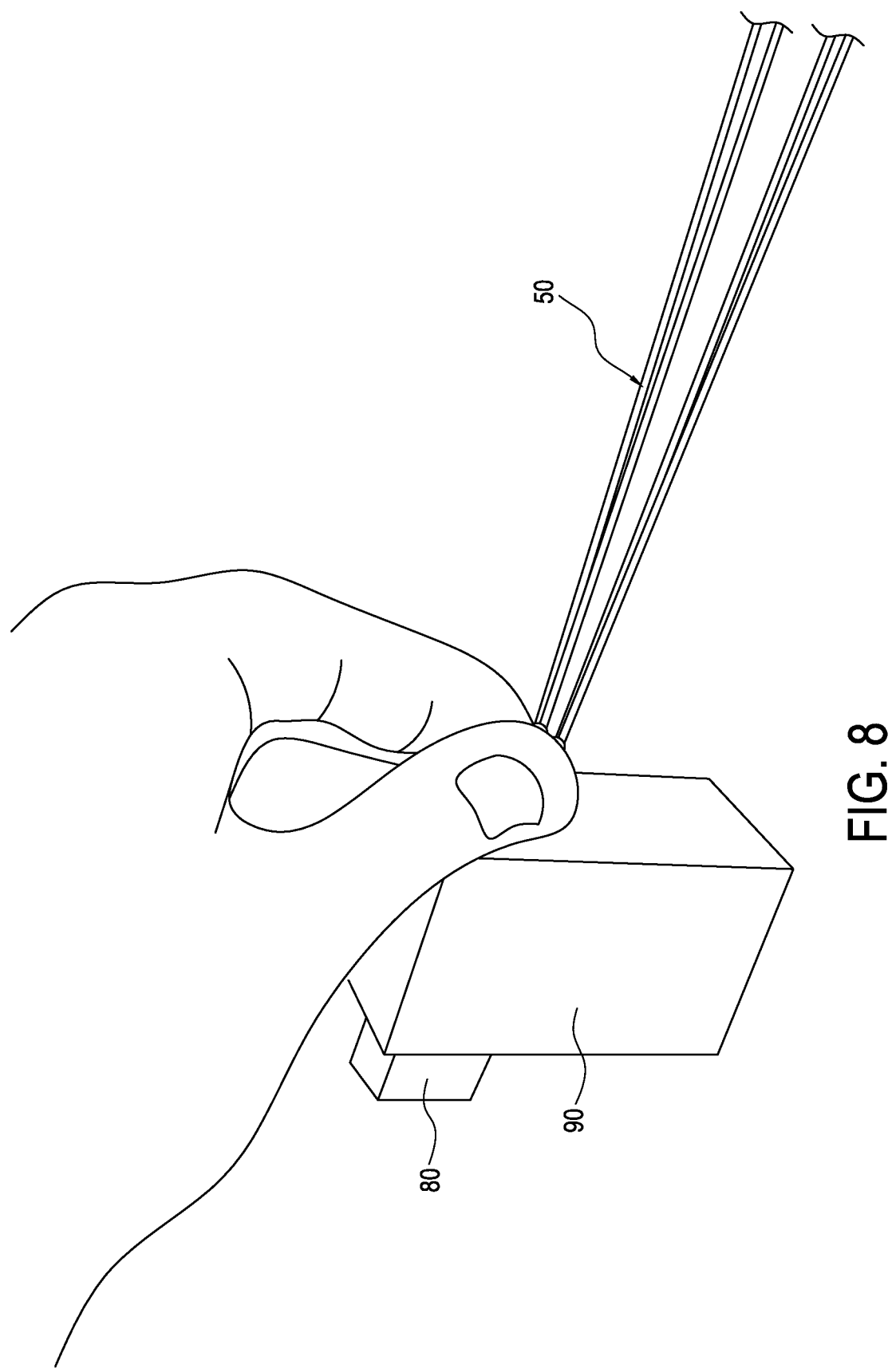

FIG. 7 illustrates connecting the cerclage sutures 20, 30 of assembly 10 to obtain tensionable cerclage construct 50 (shown in FIGS. 2 and 3). Once tails 25, 35 have exited the second bone block or bone 90, cerclage strands 20, 30 are connected to each other (joined or interconnected to each other) outside the bone tunnels. Cerclage strands 20, 30 may be interconnected or joined to each other through connecting mechanisms 22, 33 to join/secure one of the strands to the other of the strands. The strands may be also joined/interconnected/connected by splicing, fusion, gluing, knotting, or by other methods, or combined methods, known in the art.

Figure 9:
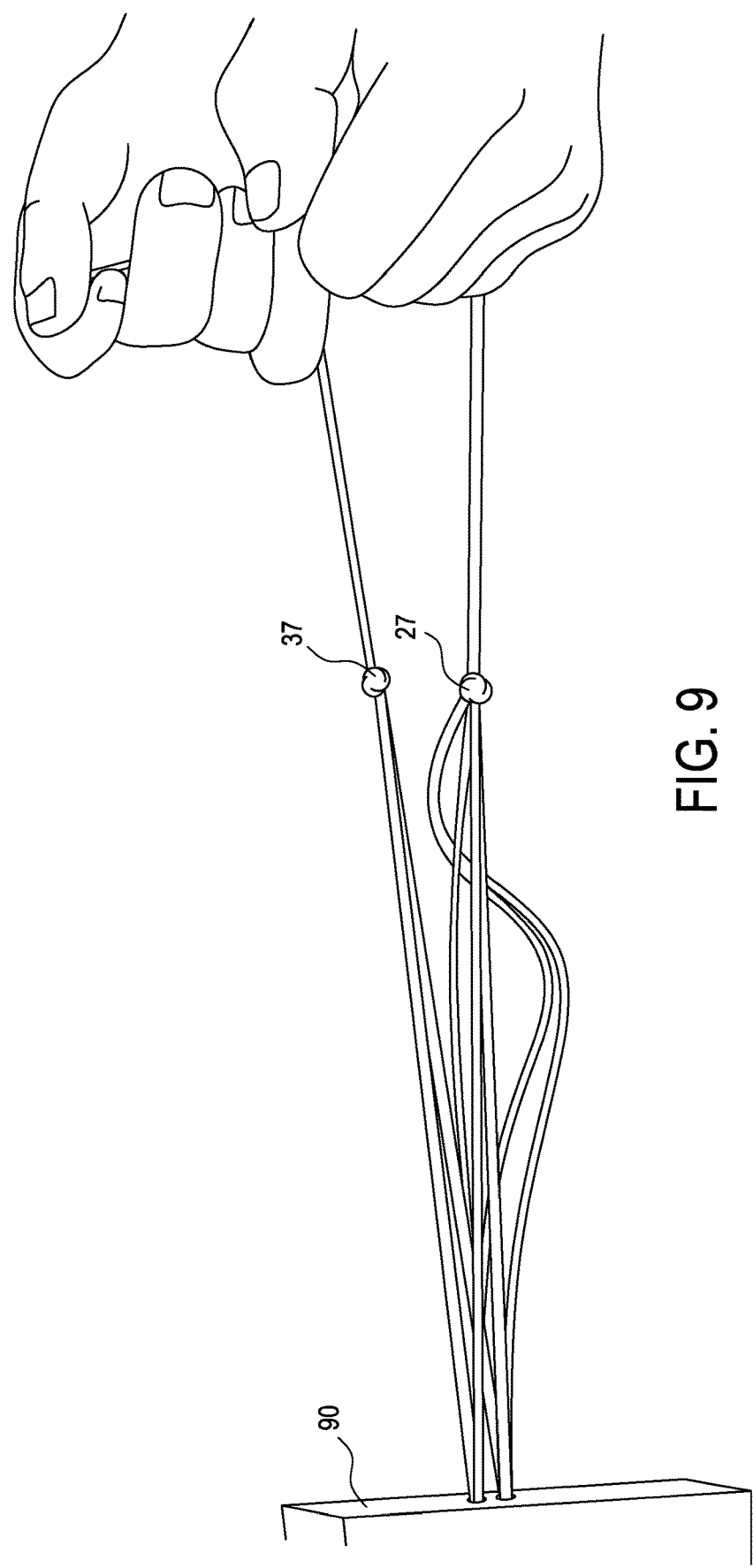
Figure 10:
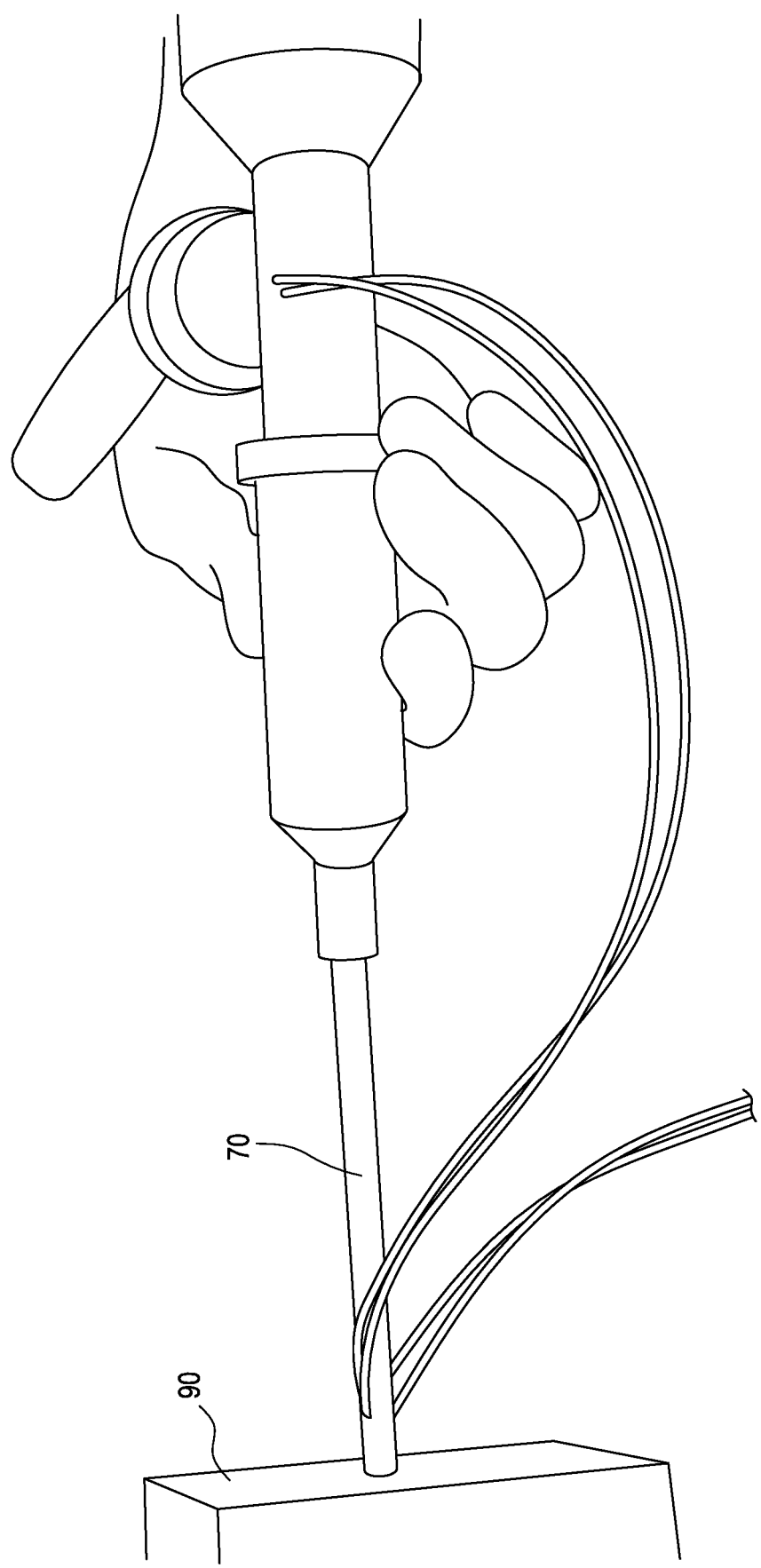
Figure 12:
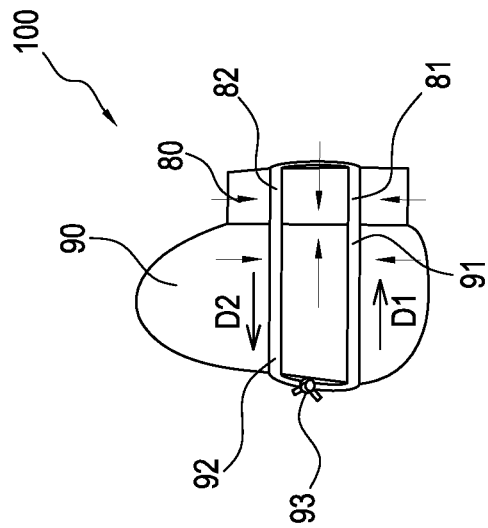
Figure 11:
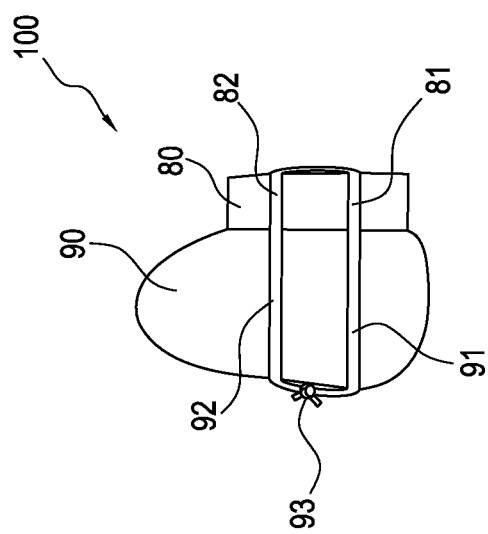

FIG. 9 shows tensioning/pulling of the strands of the cerclage construct 50 by hand and in a symmetric manner. Tensioning and pulling of the strands allows knots 27, 37 to engage the bone tunnels 91, 92 on the glenoid surface opposite to the glenoid surface abutting the bone block 80. FIG. 10 shows tensioner 70 employed to tension the strands subsequent to cutting of the single tail/swedge 25, 35. Knots 93 are formed as desired and as necessary, to secure the released strands to second bone 90 and obtain final repair 100 (FIGS. 11 and 12). FIG. 12 illustrates final repair 100 which is about similar to that of FIG. 11 but differs in that it illustrates the forces and direction of forces relative to the two bone blocks or bones 80, 90 that are connected. Tissue compression and fixation is achieved with no metal constructs and points that could cause irritation of tissue and final repair.

FIGS. 13-15 illustrate exemplary cerclage repair 101 formed of a plurality of cerclage assemblies and cerclage constructs of the present disclosure, to attach a plurality of bone blocks or bones to other bone blocks or bones. For example, FIG. 15 illustrates repair 101 with three exemplary cerclage assemblies 10 and three cerclage constructs 50a, 50b, 50c of the present disclosure. FIG. 13 illustrates constructs 50a, 50b securing two bone blocks or bones 80a, 80b to another bone block or bone 90 (for example, glenoid 90), and with a third cerclage construct 50c securing a third bone block or bone 80c to bone block or bone 90, for final repair 101 (FIG. 15). Cerclage constructs 50a, 50b, 50c may all be similar to the others or dissimilar, and may be formed of same or different cerclage strands and flexible strands. FIG. 15 also illustrates cerclage strands 20, 30 looping on the surface side of the bone block 80 (the base of the "U" shaped structure formed by the cerclage strands) and knots 93 formed on the surface of the glenoid 90. One or more knots 93 may be provided on each repair site.

FIGS. 18-20 illustrate another exemplary cerclage repair 200 formed of two simple flexible strands 120, 130 which may be in the form of simple sutures, strands, strings, flexible materials 120, 130. FIG. 18 illustrates suture 120 doubled and looped to form loop 124 and two free suture limbs. The two free suture limbs of each of the looped strands 120, 130 are both passed through the loop 124, 134 of the other double looped suture 120, 130, to make a knot. The free ends are placed into the opposite suture loop. The two suture strands may have different colors (for visual differentiation) and/or different materials, configurations and/or characteristics.

FIG. 19 illustrates the two double looped suture strands 120, 130 each with a loop 124, 134 passed through bone tunnels formed within a first bone or bone graft 80 to be attached to a second bone or bone graft 90, and before the step of interconnecting/connecting/joining the two strands. FIG. 20 illustrates the repair 200 secured by one or more knots 193 placed on a surface of second bone or bone graft 90.

Flexible strands 20a, 20b, 30a, 30b, 120, 130 and cerclage strands 20, 30 may be made of any known monofilament fiber such as monofilament suture, and portions of it may include fibers of ultrahigh molecular weight polyethylene (UHMWPE) or the FiberWire® suture (disclosed in U.S. Pat. No. 6,716,234, the disclosure of which is hereby incorporated by reference in its entirety herein). FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

Flexible strands 20a, 20b, 30a, 30b, 120, 130 and cerclage strands 20, 30 may be also formed partially or totally of suture tape, for example, flat suture tapes such as Arthrex FiberTape®, which is a high strength suture tape that is braided and rectangular-like in cross section and as disclosed in U.S. Pat. No. 7,892,256, the disclosure of which is incorporated by reference in its entirety herein.

Flexible strands 20a, 20b, 30a, 30b, 120, 130 and cerclage sutures 20, 30 may be also formed of a stiff material, or combination of stiff and flexible materials, depending on the intended application. The flexible strands 20a, 20b, 30a, 30b, 120, 130 and cerclage sutures 20, 30 may be also coated and/or provided in different colors. The cerclage constructs and assemblies of the present disclosure can be used with any type of flexible material or suture or tape that allows interconnecting/linking with other flexible material or materials.

Flexible strands 20a, 20b, 30a, 30b, 120, 130 and cerclage strands 20, 30 may be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture, loop security, pliability, handleability or abrasion resistance, for example.

Flexible strands 20a, 20b, 30a, 30b, 120, 130 and cerclage sutures 20, 30 may be also provided with tinted tracing strands, or otherwise contrast visually with other areas/regions of the construct, which remains a plain, solid color, or displays a different tracing pattern, for example. Various structural elements of flexible strands 20a, 20b, 30a, 30b, 120, 130 of cerclage construct 50 may be visually coded, making identification and handling of the sutures and ends simpler. Easy identification of suture in situ is advantageous in surgical procedures.

The cerclage construct 50 of the present disclosure may be part of a kit that may include cerclage strands such as FiberTape® and TigerTape™ cerclage sutures, various passing instruments, tensioner, handle, and instrument tray.

A bone cerclage construct 50 comprises a plurality of flexible strands 20, 30, 20a, 20b, 30a, 30b, 120, 130 extending through a plurality of bones 80, 80a, 80b, 80c, 90 or bone blocks or bone grafts, wherein at least two of the plurality of flexible strands 20a, 20b, 30a, 30b, 120, 130 are connected to each other. The plurality of flexible strands 20, 30, 20a, 20b, 30a, 30b, 120, 130 extends through a first bone tunnel 91, 81 in a first direction D1, and through a second bone tunnel 82, 92 in a second direction D2.

A bone cerclage construct 50 comprises a plurality of cerclage strands 20, 30, 20a, 20b, 30a, 30b, 120, 130 with a connecting mechanism 22, 33, 24, 124 connecting at least two of the plurality of cerclage strands. At least one of the plurality of cerclage strands 20, 30 may be formed of flexible strands 20a, 20b, 30a, 30b terminating in a single tail 25, 35. Each of the cerclage strands 20, 30 may comprise two suture tapes 20a, 20b and 30a, 30b terminating in a single tail 25 and 35.

A bone cerclage assembly 10 comprises two flexible strands 20, 30, 20a, 20b, 30a, 30b, 120, 130; and a shuttling device 40, 65, 67, 69 for passing the flexible strands through one or more first bones or bone grafts 80, through one or more second bones or bone grafts 90, and through a connecting mechanism of the two flexible strands, to interconnect the two flexible strands and form a non-metallic, tensionable, cerclage construct 50. The connecting mechanism of each of the two flexible strands may be a pre-tied knot 124, 134 on each of the two flexible strands. The shuttling device 40 may be a Nitinol loop. The two flexible strands may be sutures or tapes.

A method of cerclage repair 100, 101, 200 comprises passing a plurality of cerclage strands 20, 30, 20a, 20b, 30a, 30b, 120, 130 through a first bone 90 and a second bone 80; interconnecting the plurality of cerclage strands 20, 30, 20a, 20b, 30a, 30b, 120, 130 to form a tensionable, flexible cerclage construct 50; and pulling on the cerclage strands of the cerclage construct to approximate the first bone 90 to the second bone 80. The method may comprise drilling a first tunnel 91, 81 through the first bone 90 and the second bone 80; drilling a second tunnel 92, 82 through the first bone 90 and the second bone 80, wherein the first tunnel is spaced apart from the second tunnel by a distance "d"; passing the plurality of cerclage strands 20, 30, 20a, 20b, 30a, 30b, 120, 130 through the first tunnel 91, 81 in a first direction D1; and passing the plurality of cerclage strands 20, 30, 20a, 20b, 30a, 30b, 120, 130 through the second tunnel 92, 82 in a second direction D2 which is different from the first direction D1. The strands may be connected by a simple knot. The strands may be connected by a splicing one strand into or onto another strand. The strands may be connected by bonding, fusion, gluing, knotting, or similar method.

A bone cerclage construct 50 comprises a plurality of cerclage sutures 20, 30 with a connecting mechanism 22, 33 connecting at least two of the plurality of cerclage sutures 20, 30. The plurality of cerclage sutures 20, 30 may each comprise a plurality of flexible strands 20a, 20b, 30a, 30b terminating in a single tail 25, 35 at one end of the cerclage sutures. The single tail allows the cerclage sutures to pass through bone tunnels formed within bone blocks and/or bones. The cerclage sutures 20, 30 may include two suture tapes 20a, 20b, 30a, 30b terminating in a single tail 25, 35 and that are interconnected to each other by connecting mechanism 22, 33.

A bone cerclage assembly 10 comprises two cerclage strands 20, 30, each of the two cerclage strands 20, 30 comprising two suture tapes 20a, 20b, 30a, 30b terminating in a single tail 25, 35 at one end of each of the two cerclage strands 20, 30; and two shuttling devices 40 for passing the single tail 25, 35 of each of the two cerclage strands 20, 30 through a connecting mechanism 22, 33 of the other of the two cerclage strands to interconnect the two cerclage strands and form a non-metallic, tensionable, cerclage construct 50.

An exemplary method of tissue repair may comprise inter alia the steps of passing cerclage assembly 10 with a plurality of flexible strands through bone tunnels or passages formed within first and second bones or bone blocks; and securing the cerclage assembly 10 to the first and second bones or bone blocks without any metal or metal-like material. The cerclage assembly 10 may be secured outside of the first and second bones or bone blocks by one or more static knots.

A method of cerclage repair 100, 101, 200 comprises the steps of passing a plurality of cerclage strands 20, 30, 20a, 20b, 30a, 30b, 120, 130 through tunnels 81, 82, 91, 92 formed within a first bone 80 and a second bone 90; interconnecting the plurality of cerclage strands 20, 30, 20a, 20b, 30a, 30b, 120, 130 to form a tensionable, flexible cerclage construct 50; and pulling on the cerclage strands 20, 30, 20a, 20b, 30a, 30b, 120, 130 of the cerclage construct 50 to approximate and secure the first bone 80 to the second bone 90.

The present disclosure provides a cerclage suture mechanism which is used to hold the bones together. The novel cerclage suture mechanism eliminates metal or absorbable screws or suture-button constructs (suture and button constructs; suture/button constructs) that are used to hold the bones together. Using the cerclage sutures makes the technique easier and more reproducible, while helping to avoid intra-operative and post-operative complications.

Traumatic glenohumeral dislocation or chronic glenohumeral dislocation/subluxation can cause damage to or fracture the glenoid rim. The resulting bone loss leads to anterior instability that cannot be corrected with soft tissue/labral repair alone. Thus, a preshaped bone graft transfer is performed based on preoperative diagnostic imaging and arthroscopic evaluation of percentage of bone loss. The increase in bone area by securing the bone graft to the glenoid leads to a stabilized glenohumeral joint. By securing the bone graft with two cerclage sutures, the surgeon simplifies the procedure in comparison to existing techniques and avoids intra- and post-op complications associated with metal components. A unique feature of using two cerclage sutures (such as two FiberWire® sutures or two FiberTape® cerclage sutures) is the ability to interconnect one to the other, thus providing the ability for symmetrical tensioning of both sutures.

The disclosure provides a bone block cerclage and method of bone cerclage. The disclosure provides higher, adjustable compression of the bone block; fixation without metal components/screws; less invasive since smaller bone tunnels are needed; simplified technique.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A method of cerclage repair comprising:
  passing a plurality of cerclage strands through a first bone and a second bone;
  interconnecting the plurality of cerclage strands to form a tensionable, flexible cerclage construct, wherein the tensionable, flexible cerclage construct consists essentially of the plurality of cerclage strands;
  pulling on the cerclage strands of the cerclage construct to approximate the first bone to the second bone; and
  symmetrically tensioning the cerclage strands.

2. The method of claim 1, further comprising the steps of:
  drilling a first tunnel through the first bone and the second bone;
  drilling a second tunnel through the first bone and the second bone, wherein the first tunnel is spaced apart from the second tunnel;

passing the plurality of cerclage strands through the first tunnel in a first direction; and passing the plurality of cerclage strands through the second tunnel in a second direction which is different from the first direction.

3. The method of claim 1, wherein the step of interconnecting the plurality of cerclage strands further comprises passing a flexible strand of one of the plurality of cerclage strands through a connecting mechanism of another flexible strand of another of the plurality of cerclage strands.

4. The method of claim 3, wherein the connecting mechanism is a loop, an eyelet, a half-knot, a knot, a raking hitch knot, or a splice.

5. The method of claim 1, wherein the first bone is glenoid and the second bone is a bone graft or bone block to be attached to the glenoid.

6. The method of claim 1, wherein the plurality of cerclage strands consists of two sutures.

7. The method of claim 1, wherein each of the plurality of cerclage strands consists of suture tapes terminating in a single end or tail.

\* \* \* \* \*